United States Patent [19]

Kruper, Jr. et al.

[11] Patent Number: 4,746,735

[45] Date of Patent: May 24, 1988

[54] REGIOSPECIFIC ARYL NITRATION OF MESO-SUBSTITUTED TETRAARYLPORPHYRINS

[75] Inventors: William J. Kruper, Jr., Sanford; Thomas A. Chamberlin, Midland, both of Mich.

[73] Assignee: The Dow Chemical Company, Midland, Mich.

[21] Appl. No.: 933,503

[22] Filed: Nov. 21, 1986

[51] Int. Cl.$^4$ .......................................... C07D 487/22
[52] U.S. Cl. .................................................... 540/145
[58] Field of Search ....................................... 540/145

[56] References Cited

FOREIGN PATENT DOCUMENTS 3045 5/1984 Australia .

OTHER PUBLICATIONS

Johnson et al., Chem. and Ind. (1975), p. 351.
Baldwin et al., Tetrahedron, vol. 38 (1982), pp. 685–692.
Catalano et al., J. Chem. Soc. Chem. Commun., (1984), pp. 1535–1536.
Evans et al., J. Chem. Soc.: Perkin Trans. I, (1978), pp. 768–773.
Hasegawa et al., Eur. Polymer J., vol. 14 (1978), pp. 123–127.
Tsuchida et al., Macromolecules, vol. 11, No. 5 (1978), pp. 947–955.
Gonzalez et al., Can. J. Chem., vol. 63 (1985), pp. 602–608.
Little et al., J. Het. Chem., vol. 12 (1975), pp. 343–349.
Winkleman et al., Cancer Research, vol. 27 (1967), pp. 2060–2064.
Winkleman et al., Cancer Research, vol. 22 (1961), pp. 589–596.
Robinson et al., J. Nucl. Med., vol. 27 (1986), pp. 239–242.
Busby et al., Can. J. Chem., vol. 53 (1975), pp. 1554–1555.
Srivastava et al., J. Org. Chem., vol. 38 (1973), p. 2103.
Tsuchida, J. Macromol, Sci.-Chem., vol. A13, No. 4 (1979), pp. 545–571.

*Primary Examiner*—Richard L. Raymond
*Attorney, Agent, or Firm*—S. Preston Jones; Ronald G. Brookens

[57] ABSTRACT

A process for the nitration of a tetraarylporphyrin compound such as tetraphenylporphyrin by use of a nitrating agent in a suitable solvent in the presence of an amount of sulfuric acid that is less than equimolar relative to the amount of nitrating agent.

32 Claims, No Drawings

REGIOSPECIFIC ARYL NITRATION OF MESO-SUBSTITUTED TETRAARYLPORPHYRINS

BACKGROUND OF THE INVENTION

Substituted tetraarylporphyrins, particularly monofunctionalized porphyrins, are known to be useful in the area of facilitated transport of oxygen as demonstrated by Hasegawa et al. in *Eur. Polymer J.* 1978, 14, 123–127. Such compounds are also known to serve as valuable precursors to tumor imaging agents and therapeutics (radiopharmaceuticals) as taught by Schmitt et al. in Australian Patent Application 3045/83 to F. Hoffman-LaRoche & Co., 1983. Monofunctionalized porphyrins have also been utilized in the cyclodextrin catalysis area (see Gonzalez et al., *Can. J. Chem.* 1985, 63, 602).

Known methods for synthesis of nitro-substituted tetraarylporphyrins provide low yields of desired product and require difficult isolation procedures. For example, Rothmund condensations in which two different aromatic aldehydes are condensed with pyrrole result in yields less than 3% of desired product (Hasegawa et al., *Eur. Polymer J.* 1978, 14, 123–127). The Hasegawa et al. process can be summarized as follows

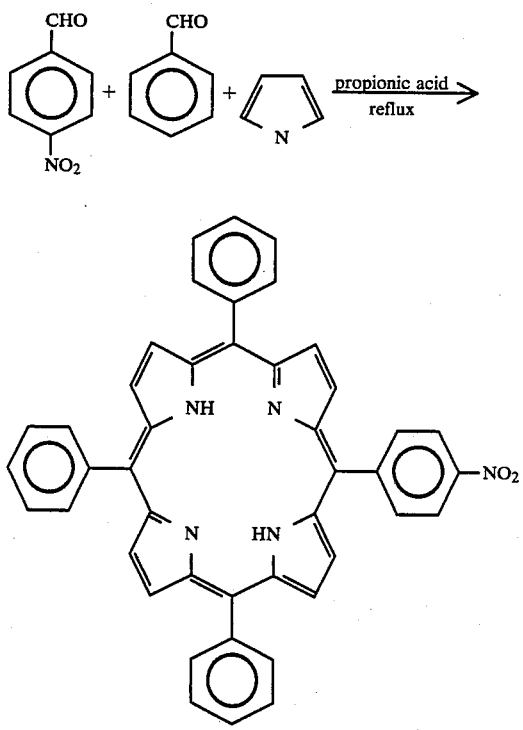

(I)

In the Hasegawa et al. process five different porphyrins were produced in the crossed condensation of benzaldehyde and p-nitrobenzaldehyde with pyrrole. The isolation of the desired product (compound of formula I) required repetitive silica gel chromatography. The low yields and purification problems have been noted by others who have employed crossed-condensation methodologies in the synthesis of functionalized porphyrins (see Gonzalez et al. *Can. J. Chem.* 1985, 63, 602; Little et al. *J. Heterocycle. Chem.* 1975, 12, 343; and Schmidt et al. Australian Patent Application 3045/83 to F. Hoffman-LaRoche & Co., 1983).

The above-noted problems have prompted others to consider direct peripheral functionalization of symmetrical tetraarylporphyrins. The electrophillic addition of sulfuric acid to the phenyl ring of tetraphenylporphyrin is one of the few examples in the prior art of aryl group modification without concomitant attack on the macrocycle ring (see Winkelman et al., *Cancer Research* 1967, 27, 2060; Winkelman, *Cancer Research* 1961, 22, 589; Robinson et al., *J. Nucl. Med.* 1986, 27, 239; Busby et al., *Can. J. Chem.* 1975, 53, 1554; and Srivastava et al., *J. Org. Chem.* 1973, 38, 2103). However, such processes result in substitution at all four phenyl groups during the course of the reaction and stepwise sulfonation is difficult to control.

It is taught in the art that direct nitration of aryl moieties requires the presence of a substantial amount of sulfuric acid as a catalyst in order for nitration to occur (see, for example, Morrison and Boyd, *Organic Chemistry*, 3rd ed., 1973, Allyn and Bacon, Inc., Boston, pp. 337–371). With respect to direct nitration of a tetraarylporphyrin, substitution at the aryl position has heretofore been unknown. When such direct nitration had been attempted, products substituted at either the beta position or the meso position have been produced. The above-noted ring positions are illustrated below for tetraphenylporphyrin

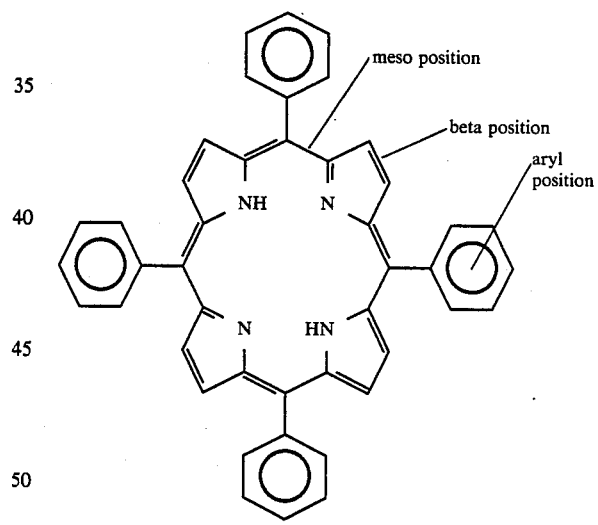

It has been demonstrated that the sole route of nitro substitution for prior art processes occurs at the beta position of the macrocycle ring under a variety of free radical oxidation conditions (see Baldwin et al., *Tetrahedron*, 1982, 38, 685; Crossley et al., *J. Chem. Soc. Chem. Commun.*, 1984, 1535; and Evans et al., *J. Chem. Soc.: Perkin Trans. I*, 1978, 768). In addition, Johnson et al. (*Chemistry and Industry*, 1975, 351) have reported that sulfuric acid catalyzed nitration of tetraphenylporphyrin has led to tetraphenylporphyrin substituted with a nitro moiety at the beta position in mixture with two meso-substituted products having the following formulae:

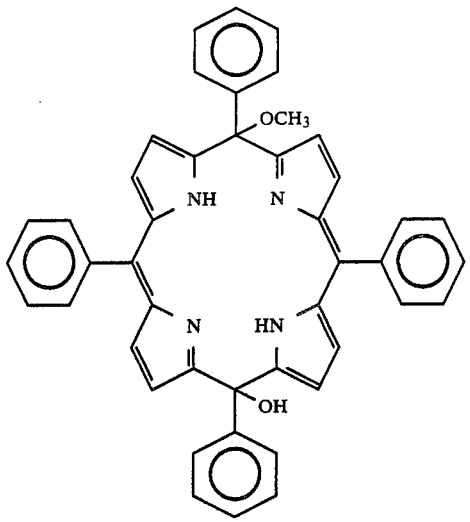

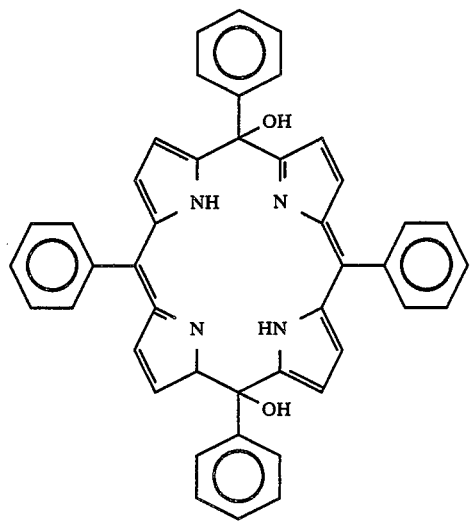

There are no known processes in the prior art for direct mono-nitration and/or stepwise nitration of tetraarylporphyrins at the peripheral aryl position(s). The present invention provides for such a process.

SUMMARY OF THE INVENTION

The present invention is directed to a process for the nitration of a tetraarylporphyrin compound at one or more peripheral unsubstituted aryl positions. The present process greatly increases the yield of desired product and also provides a product that requires much less cumbersome and expensive purification procedures than prior art processes. The present process comprises contacting a tetraarylporphyrin compound of the formula

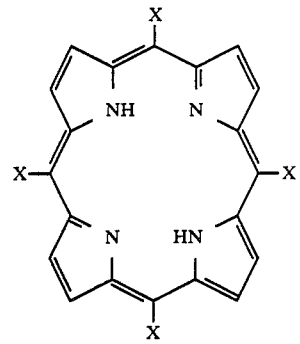

(II)

or a metallo derivative thereof wherein each X represents an aryl moiety each of which is independently substituted with up to four same or different substituents selected from the group consisting of aryl, alkyl, halo, alkylaryl, alkoxy, or carboalkoxy, with a nitrating agent in a suitable solvent in the presence of an amount of sulfuric acid that is less than equimolar relative to the amount of nitrating agent under conditions such that at least one peripheral aryl moiety of the tetraarylporphyrin is nitrated.

As used herein, the term "aryl" refers to aromatic moieties containing up to 18 carbon atoms such as phenyl, biphenyl, naphthyl, and anthryl; the term "alkyl" refers to straight chain, branched chain, or cyclic alkyl moieties containing up to 10 carbon atoms; and the term "halo" refers to fluoro, chloro, bromo or iodo. Preferred alkyl moieties contain one to four carbon atoms; preferred halo moieties are chloro and bromo; preferred aryl moieties are phenyl and naphthyl; and a preferred alkoxy moiety is methoxy.

DETAILED DESCRIPTION OF THE INVENTION

It has been discovered that the direct nitration of the peripheral aryl moieties occurs in the presence of an amount of sulfuric acid that is less than equimolar relative to amount of nitrating agent. It is preferred that the process proceed in the absence of, or in the substantial absence of, sulfuric acid. If sulfuric acid is present competitive macrocycle nitration and/or hydroxylation will occur. As used herein the phrase "in the substantial absence of sulfuric acid" refers to conducting the process of the present invention in the presence of an amount of sulfuric acid no greater than that amount that will allow for less than about 4% of the theoretical maximum yield of desired product. The desired product resulting from the process of the present invention is the compound of formula II that has at least one peripheral aryl moiety nitrated. As used herein, the phrase "peripheral aryl moiety" refers to the aryl moiety bonded directly to the meso position of the macrocycle.

Nitrating agents useful in the present invention are concentrated or fuming nitric acid and/or nitronium fluoroborate. A preferred nitrating agent is nitric acid having a specific gravity of between about 1.1 and about 1.6; more preferred is nitric acid having a specific gravity of between about 1.4 and about 1.6; and most preferred is nitric acid having a specific gravity of about 1.6.

Suitable solvents for the process of the present invention are those solvents that are substantially inert to the reaction and are supportive of substrate solubility. Examples of suitable solvents include acetic acid, propionic acid, and halogenated hydrocarbons such as chloroform, methylene chloride, perchloroethylene, and 1,1,2 or 1,1,1-trichloroethane. Preferred solvents are acetic acid, methylene chloride, and chloroform; most preferred is chloroform. In general, halogenated hydrocarbons will favor mono- or di-nitration and acid solvents will favor tri- or tetra-nitration.

The process of the present invention proceeds in such a manner that at least about 4% of the theoretical maximum yield of desired product is formed; preferred is that at least about 20% of the theoretical maximum yield of desired product is formed; and most preferred is that at least about 50% of the theoretical maximum yield of desired product is formed.

Temperature and pressure for the process of the present invention are not known to be particularly critical. However, about atmospheric pressure is preferred and a temperature range of from about −25° C. to about 50° C. is preferred; a more preferred temperature range is from about −10° C. to about 25° C.

The process is allowed to proceed for a reaction time sufficient to obtain the desired yield of desired product. Such a reaction time is typically from about 20 minutes to about 5 hours. A preferred reaction time is from about 1 hour to about 3 hours.

A molar excess of nitrating agent relative to the compound of formula II is required. Larger amounts of nitrating agent relative to the compound of formula II will favor multiple nitrations; that is, nitrating more than one aryl moiety. For tri-nitration in an acid solvent, a large molar excess of nitrating agent relative to the porphyrin compound may be required, e.g., in the range of about 300:1. A preferred molar ratio of reactants for mono- or di-nitration (nitrating agent:compound of formula II) is from about 10 to about 32:1; more preferred for mono-nitration is from about 16 to about 20:1; and more preferred for di-nitration is from about 24 to about 32:1.

In the process of the present invention each peripheral aryl moiety can be nitrated at no more than one unsubstituted peripheral aryl position. As used herein, "mono-nitration" means that one peripheral aryl moiety is nitrated with one nitro functionality; "di-nitration" means that two peripheral aryl moieties are each nitrated with one nitro functionality; "tri-nitration" means that three peripheral aryl moieties are each nitrated with one nitro functionality; and "tetra-nitration" means that all four peripheral aryl moieties are each nitrated with one nitro functionality. For the present invention mono-, di- and tri-nitration are preferred; most preferred is mono-nitration.

The present invention also contemplates that the tetraarylporphyrin compound can be in the form of a metallo derivative. Metallo derivatives of the compound formula II have the formula

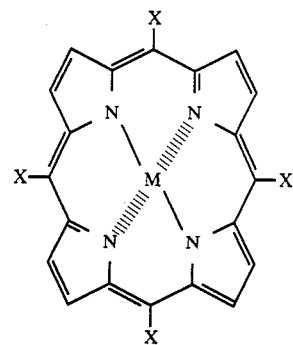

wherein M is a metal atom such as Zn, Rh, Ni, Cu, or Pd.

A preferred process of the present invention comprises contacting a compound of the formula

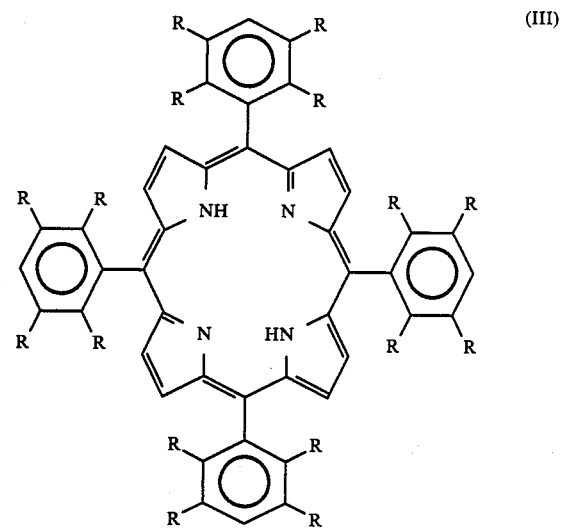

(III)

wherein each R independently represents hydrogen, aryl, alkyl, halo, alkylaryl, alkoxy, or carboalkoxy with nitric acid in a suitable solvent in the presence of an amount of sulfuric acid that is less than equimolar relative to the amount of nitric acid under conditions such that at least one peripheral aryl moiety is nitrated at the para position.

It is also preferred that the process of the present invention proceed in or under an inert atmosphere such as nitrogen or argon.

Specific tetraarylporphyrins useful in the process of the present invention include tetraphenylporphyrin, tetratolylporphyrin, tetramesitylporphyrin, tetranaphthylporphyrin, tetra-3-chlorophenylporphyrin, tetra-3-methoxyphenylporphyrin, and tetraanthracenylporphyrin.

The nitrated porphyrins produced by the process of the present invention can optionally be reduced to the corresponding amino derivatives using procedures known in the art. Therefore another embodiment of the invention includes such additional reduction step.

The following examples are merely illustrative, and are not intended as a limitation on the invention.

EXAMPLE 1

Mono-5-(4-nitrophenyl)-tris-10,15,20-(phenyl)porphyrin from direct nitration of tetraphenylporphyrin in the absence of sulfuric acid Tetraphenylporphyrin (2.0 grams (g), 3.25 millimoles (mmoles), obtained from Midcentury Coordination Chemicals, Posen, Ill.) was dissolved in 200 milliliters (ml) of pentene stabilized chloroform under nitrogen. The resulting solution was stirred and fuming nitric acid (3.4 g, 54 mmole, Baker reagent grade, specific gravity 1.6) was added to the solution while keeping the temperature at 0°–5° C. by use of a pressure equalizing dropping funnel over a two hour period. The reaction was monitored at intervals by Thin Layer Chromatography (TLC) to insure total conversion of starting material to product using chloroform/silica plates (obtained from Analtech). After the two hour reaction period the reaction mixture turned dark green. The dark green reaction mixture was extracted with 5×300 ml portions of water and dried over magnesium sulfate and sodium carbonate. The resulting solution was concentrated to 70 ml and was applied to a silica chromatography column (18 inch×1 inch Aldrich 62 grade 60-200 A mesh) using chloroform as an eluent. Fractions containing only the mono-nitro derivative were combined and rotary evaporated giving mono-5-(4-nitrophenyl)-tris-10,15,20-(phenyl)porphyrin in 55% yield (1.20 g, 18.1 mmole). Fractions containing only the di-nitro derivative were combined and rotary evaporated giving bis-5,10-(4-nitrophenyl)bis-15,20-(phenyl)porphyrin in 5% yield. The structures were confirmed by infrared (IR), mass sprectroscopy (MS), proton nuclear magnetic resonance (PMR), and 13C nuclear magnetic resonance (CMR).

Anal. Calcd. for $C_{44}H_{29}NO_2$: C, 80.09; H, 4.43; N, 10.61. Found: C, 79.8; H, 4.46; N, 10.56.

EXAMPLE 2

Bis-5,10-(4-nitrophenyl)-bis-15,20-(phenyl)porphyrin from tetraphenylporphyrin in the absence of sulfuric acid Tetraphenylporphyrin (500 milligrams (mg), 0.813 mmole) was dissolved in 75 ml of chloroform and fuming nitric acid (1.5 g, 23.8 mmole) was added dropwise with stirring (at 0°–5° C.) until TLC analysis showed total conversion of mono derivative (which took approximately 2 hours). Chromatography of the crude porphyrinic fraction (1 inch×14 inch silica column) using chloroform as an eluent provided approximately 160 mg(0.227 mmole) of bis-5,10-(4-nitrophenyl)-bis-15,20-(phenyl) porphyrin as a dark purple powder (28% isolated yield); and tris-5,10,15,-(4-nitrophenyl)mono-20-(phenyl)porphyrin in 7% yield. Structures were confirmed by PMR, and MS.

Anal., Calcd., for $C_{44}H_{28}N_6O_4$: C, 74.99; H, 4.00; N, 11.92. Found: C, 74.66; H, 4.08; N, 11.30.

Using procedures substantially as described herein, additional examples were performed using tetraphenylporphyrin as a starting material. These examples are summarized in TABLE 1 below. All of these examples were carried out at 0°–5° C. except for the example using acetic acid as a solvent which was carried out at 20°–25° C. The percentages that appear in TABLE 1 refer to the yields of isolated products after chromatography.

TABLE 1

| | | | COMPOUND PRODUCED | | |
|---|---|---|---|---|---|
| EXAMPLE NUMBER | SOLVENT | EQUIVALENTS FUMING NITRIC ACID | mono-5-(4-nitrophenyl)-tris-10,15,20-(phenyl)porphyrin | bis-5,10-(4-nitrophenyl)-bis-15,20-(phenyl)porphyrin | tris-5,10,15,-(4-nitrophenyl)-mono-20-(phenyl)porphyrin |
| 3 | CHCl$_3$ | 20 | 56% | | |
| 4 | CH$_2$Cl$_3$ | 20 | 46% | | |
| 5 | CHCl$_3$ | 35 | 0% | 2% | 2% |
| 6 | acetic acid | 291 | | | 10% |

EXAMPLE 7

The following example illustrates the optional reduction step

Mono-5-(4-nitrophenyl)-tris-10,15,20-(phenyl) porphyrin (2.50 g, 3.79 mmole) was dissolved in 80 ml of concentrated hydrochloric acid under nitrogen. Tin (II) chloride dihydrate (2.6 g, 11.5 mmole) was added to the solution and the reaction was heated to 65° C. for one hour. The resulting solution was cooled and added to 300 ml of cold water and was adjusted to pH 8 with concentrated ammonium hydroxide which resulted in a two phase solution (aqueous and organic). The aqueous phase was extracted with 6×300 ml portions of chloroform which were combined and dried over magnesium sulfate. The organic phase was concentrated on a rotary evaporator to 100 ml and this solution was chromatographed through a 14 inch×1 inch silica column (Aldrich 62 grade) using methylene chloride as an eluent. The first and only band eluting from the column was the desired 5-(4-aminophenyl)-10,15,20-(triphenyl)porphyrin which was obtained in 74% yield. The structure was confirmed by PMR, and MS.

Anal. Calcd. for $C_{44}H_{31}N$: C, 83.9; H, 4.93; N, 11.28. Found: C, 84.13; H, 4.86; N, 11.20.

What is claimed is:

1. A process for the direct nitration of a tetraarylporphyrin compound comprising contacting a tetraarylporphyrin compound of the formula

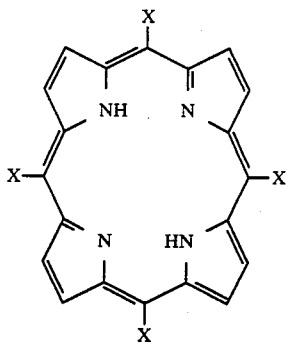

(II)

or a metallo derivative thereof wherein
each X represents an aryl moiety each of which is unsubstituted or independently substituted with up to four same or different substituents selected from the group consisting of aryl, alkyl, halo, alkylaryl, alkoxy, or carboalkoxy with a molar excess of from about 10:1 to about 300:1 of a nitrating agent in a suitable solvent in the presence of an amount of sulfuric acid that is less than equimolar relative to the amount of nitrating agent under conditions such that at least one peripheral aryl moiety is nitrated.

2. The process of claim 1 wherein the nitrating agent is nitric acid having a specific gravity of between about 1.4 and about 1.6.

3. The process of claim 1 wherein the nitrating agent is nitric acid having a specific gravity of about 1.6.

4. The process of claim 1 wherein the suitable solvent is selected from the group consisting of acetic acid, methylene chloride, and chloroform.

5. The process of claim 1 wherein the suitable solvent is chloroform.

6. The process of claim 1 wherein at least about 20% of the theoretical maximum of desired product is formed.

7. The process of claim 1 wherein at least about 50% of the theoretical maximum of desired product is formed.

8. The process of claim 1 wherein the tetraarylporphyrin compound is mono-nitrated.

9. The process of claim 1 carried out in the absence of sulfuric acid.

10. The process of claim 1 carried out in the substantial absence of sulfuric acid.

11. The process of claim 1 carried out at a temperature of from about −10° C. to about 25° C. and at about atmospheric pressure.

12. The process of claim 1 carried out in an inert atmosphere.

13. The process of claim 1 wherein the ratio of nitrating agent:tetraarylporphyrin compound is from about 10 to about 32:1.

14. The process of claim 1 wherein said tetraarylporphyrin compound is selected from the group consisting of tetraphenylporphyrin, tetratolylporphyrin, tetramesitylporphyrin, tetranaphthylporphyrin, tetra-3-chlorophenylporphyrin, tetra-3-methoxyphenylporphyrin, and tetraanthracenylporphyrin.

15. The process of claim 1 wherein the substituents on the aryl moiety are selected from the group consisting of alkyl of one to four carbon atoms, phenyl, naphthyl, bromo, chloro, and methoxy.

16. A process for the direct nitration of a tetraarylporphyrin compound comprising contacting a tetraarylporphyrin compound of the formula

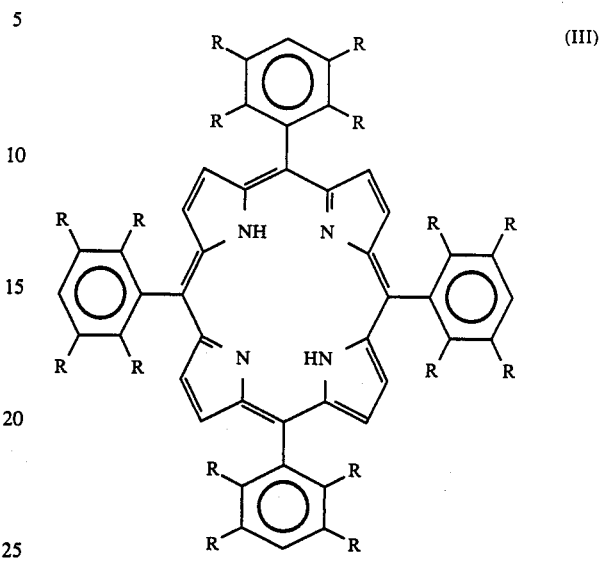

(III)

wherein each R independently represents hydrogen, aryl, alkyl, halo, alkylaryl, alkoxy, or carboalkoxy with a molar excess of from about 10:1 to about 300:1 of nitric acid in a suitable solvent in the presence of an amount of sulfuric acid that is less than equimolar relative to the amount of nitric acid under conditions such that at least one peripheral aryl moiety is nitrated at the para position.

17. The process of claim 16 wherein the nitrating agent is nitric acid having a specific gravity of between about 1.4 and about 1.6.

18. The process of claim 16 wherein the nitrating agent is nitric acid having a specific gravity of about 1.6.

19. The process of claim 16 wherein the suitable solvent is selected from the group consisting of acetic acid, methylene chloride, and chloroform.

20. The process of claim 16 wherein the suitable solvent is chloroform.

21. The process of claim 16 wherein at least about 20% of the theoretical maximum of desired product is formed.

22. The process of claim 16 wherein at least about 50% of the theoretical maximum of desired product is formed.

23. The process of claim 16 wherein the tetraarylporphyrin compound is mono-nitrated.

24. The process of claim 16 carried out in the absence of sulfuric acid.

25. The process of claim 16 carried out in the substantial absence of sulfuric acid.

26. The process of claim 16 carried out at a temperature of from about −10° C. to about 25° C. and at about atmospheric pressure.

27. The process of claim 16 carried out in an inert atmosphere.

28. The process of claim 16 wherein the ratio of nitrating agent:tetraarylporphyrin compound is from about 10 to about 32:1.

29. The process of claim 16 wherein said tetraarylporphyrin compound is selected from the group consisting of tetraphenylporphyrin, tetratolylporphyrin, tetra-3- chlorophenylporphyrin, tetra-3-methoxyphenylporphyrin, and tetramesitylporphyrin.

30. The process of claim 16 wherein the substituents on the aryl moiety are selected from the group consisting of alkyl of one to four carbon atoms, phenyl, naphthyl, bromo, chloro, and methoxy.

31. A process for preparing an amino tetraarylporphyrin which comprises contacting a tetraarylporphyrin compound of the formula

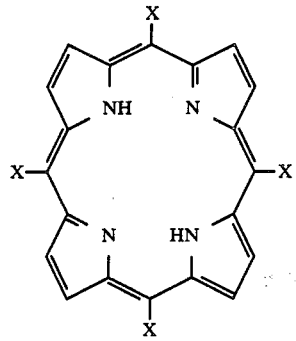

(II)

or a metallo derivative thereof wherein
each X represents an aryl moiety each of which is unsubstituted or independently substituted with up to four same or different substituents selected from the group consisting of aryl, alkyl, halo, alkylaryl, alkoxy, or carboalkoxy with a molar excess of from about 10:1 to about 300:1 of a nitrating agent in a suitable solvent in the presence of an amount of sulfuric acid that is less than equimolar relative to the amount of nitrating agent under conditions such that at least one pripheral aryl moiety is nitrated; and reducing the nitrated tetraarylporphyrin to its amino derivative.

32. A process for preparing an amino tetraarylporphyrin which comprises contacting a tetraarylporphyrin compound of the formula

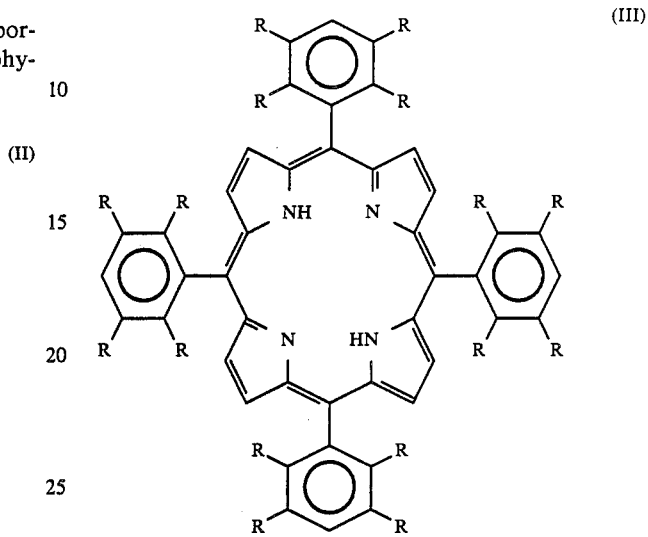

(III)

wherein each R independently represents hydrogen, aryl, alkyl, halo, alkylaryl, alkoxy, or carboalkoxy with a molar excess of from about 10:1 to about 300:1 of nitric acid in a suitable solvent in the presence of an amount of sulfuric acid that is less than equimolar relative to the amount of nitric acid under conditions such that at least one peripheral aryl moiety is nitrated at the para position; and reducing the nitrated tetraarylporphorin to its amino derivative.

* * * * *